United States Patent
Wilk

(10) Patent No.: US 7,060,021 B1
(45) Date of Patent: Jun. 13, 2006

(54) METHOD AND DEVICE FOR IMPROVING CARDIAC FUNCTION

(75) Inventor: Peter J. Wilk, New York, NY (US)

(73) Assignee: Wilk Patent Development Corporation, New York, NY (US)

(*) Notice: Subject to any disclaimer, the term of this patent is extended or adjusted under 35 U.S.C. 154(b) by 0 days.

(21) Appl. No.: 09/435,525

(22) Filed: Nov. 8, 1999

Related U.S. Application Data

(63) Continuation-in-part of application No. 09/426,744, filed on Oct. 25, 1999, now Pat. No. 6,258,021, which is a continuation-in-part of application No. 09/121,477, filed on Jul. 23, 1998, now Pat. No. 6,155,968.

(51) Int. Cl.
   *A61F 1/00* (2006.01)

(52) U.S. Cl. .......................... 600/16; 128/898

(58) Field of Classification Search ................ 600/205, 600/16–18, 37; 601/11, 153; 623/3, 11; 128/897, 898, 899; 606/153, 157, 158, 159, 606/139
See application file for complete search history.

(56) References Cited

U.S. PATENT DOCUMENTS

| | | | |
|---|---|---|---|
| 3,587,567 A | 6/1971 | Schiff | |
| 4,741,330 A * | 5/1988 | Hayhurst | 606/32 |
| 5,073,168 A | 12/1991 | Danforth | |
| 5,169,381 A | 12/1992 | Snyders | |
| 5,171,297 A | 12/1992 | Barlow et al. | |
| 5,195,970 A | 3/1993 | Gahara | |
| 5,618,307 A * | 4/1997 | Donlon et al. | 606/205 |
| 5,766,216 A | 6/1998 | Gangal et al. | |
| 5,800,528 A | 9/1998 | Lederman et al. | |
| 5,853,422 A | 12/1998 | Huebsch et al. | |
| 5,865,791 A | 2/1999 | Whayne et al. | |
| 5,879,366 A | 3/1999 | Shaw et al. | |
| 5,891,017 A * | 4/1999 | Swindle et al. | 600/205 |
| 5,928,250 A | 7/1999 | Koike et al. | |
| 5,954,747 A * | 9/1999 | Clark | 606/216 |
| 5,961,440 A | 10/1999 | Schweich, Jr. et al. | |
| 5,984,917 A * | 11/1999 | Fleischman et al. | 606/32 |
| 6,050,936 A * | 4/2000 | Schweich, Jr. et al. | 600/37 |
| 6,059,715 A * | 5/2000 | Schweich, Jr. et al. | 600/16 |
| 6,547,821 B1 * | 4/2003 | Taylor et al. | 623/3.1 |

* cited by examiner

*Primary Examiner*—Manuel Mendez
(74) *Attorney, Agent, or Firm*—R. Neil Sudol; Henry D. Coleman; William J. Sapone

(57) ABSTRACT

In a method for improving cardiac function, a compressive device is inserted into an intrapericardial space about a lower end portion of a heart. Thereafter the compressive device is operated to compress and close off lower portions of both ventricles of the heart.

20 Claims, 3 Drawing Sheets

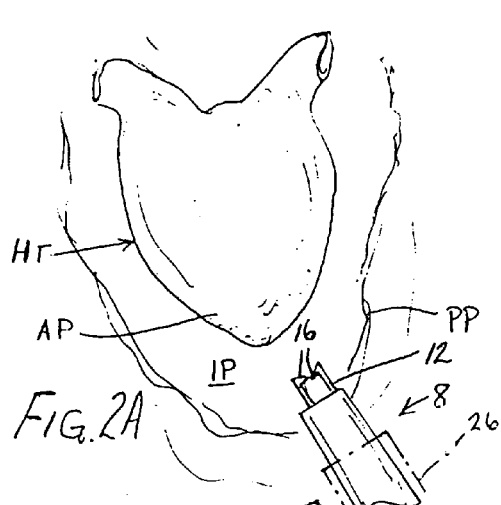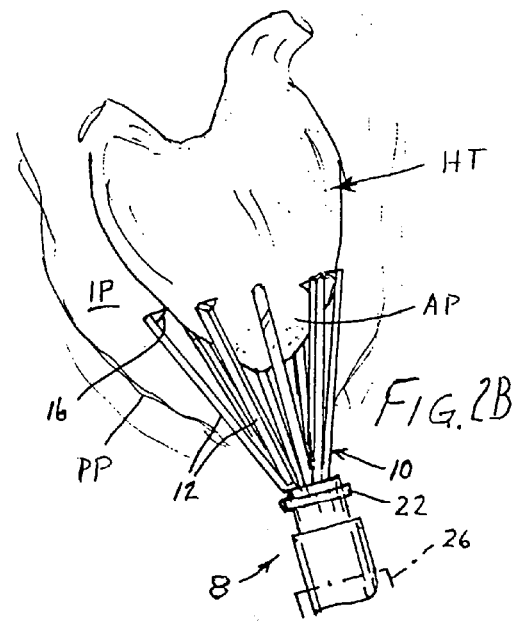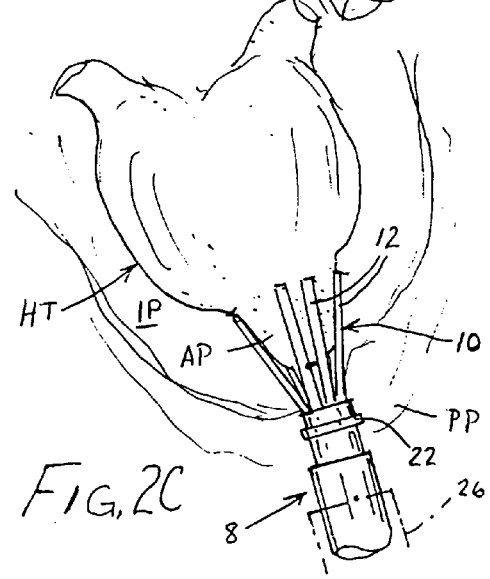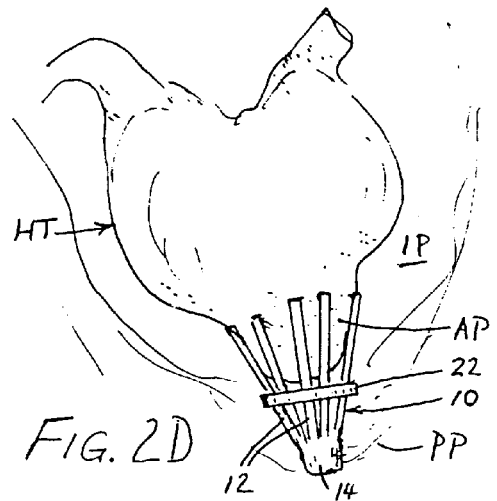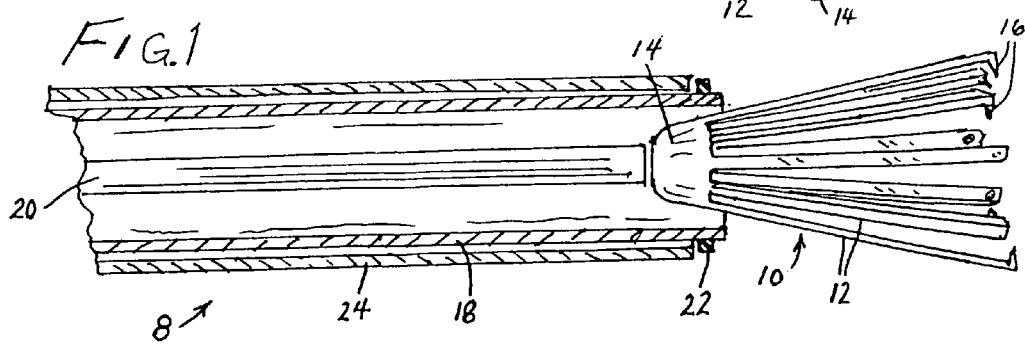

METHOD AND DEVICE FOR IMPROVING CARDIAC FUNCTION

CROSS-REFERENCE TO RELATED APPLICATION

This application is a continuation-in-part of application Ser. No. 09/426,744 filed Oct. 25, 1999, now U.S. Pat. No. 6,258,021. Application Ser. No. 09/426,744 was filed as a continuation-in-part of application Ser. No. 09/121,477 filed Jul. 23, 1998. This application is also a continuation-in-part of application Ser. No. 09/121,477, now U.S. Pat. No. 6,155,968.

BACKGROUND OF THE INVENTION

This invention relates to a method and device for improving cardiac function, particularly where there is congestive heart failure.

Congestive heart failure occurs, inter alia, where there has been a heart attack or an infection. In either case, the pumping action of the heart is impaired. In another malfunction, left ventricular hypertrophy, the myocardium of the left ventricle becomes thickened to the point of interfering with effective heart contraction.

A surgical procedure for treating congestive heart failure, developed by a doctor in Brazil, involves removing a triangular portion of a patient's heart. In this operation, approximately one-third of the patient's left ventricular muscle is removed. The result is that the smaller heart pumps more efficiently.

This new technique of course requires open heart surgery, with its attendant expense and extended convalescence.

OBJECTS OF THE INVENTION

An object of the present invention is to provide a surgical method for treating congestive heart failure.

A further object of the present invention is to provide such a surgical method which is less expensive than the above-described surgical technique.

It is another object of the present invention to provide a surgical method for treating congestive heart failure which may be implemented through minimally invasive procedures.

An additional objet of the present invention is to provide a device for implementing such a surgical method.

These and other objects of the present invention will be apparent from the drawings and descriptions herein.

SUMMARY OF THE INVENTION

A method for improving cardiac function comprises, in accordance with the present invention, inserting a tensile member into a patient, and inserting the tensile member into the patient's heart so as to compress and close off lower portions of both ventricles of the heart.

Pursuant to additional features of the invention, the method further comprises anchoring the tensile member to opposing myocardial sidewalls, the anchoring of the tensile member including placing a flanged element or a barbed element of the tensile member in contact with myocardial tissues.

In one embodiment of the present invention, the tensile member is a tack, and the inserting of the tensile member into the patient's heart includes ejecting the tack from a tubular member. The tubular member may be deployed during an open heart surgical procedure or, alternatively, via a cannula or trocar sleeve in a minimally invasive operation. In either case, the tack is applied to the heart through the intrapericardial space by aiming the tack at an outer surface of the heart.

In an alternative embodiment of the present invention, the tensile member is an at least partially elongate member such as a wire, and the inserting of the tensile member is implemented by inserting a catheter into a ventricle of the patient's heart and ejecting the tensile member from the catheter into the patient's myocardium so that the tensile member is anchored to the myocardium. Subsequently, tension is exerted on the tensile member to pull opposing walls of the patient's heart towards one another so as to compress and close off lower portions of both ventricles of the heart.

Where the tensile member is provided with at least one barb at a leading end, the attaching of the tensile member to the patient's heart includes embedding the barb in the patient's heart.

In this alternative embodiment of the present invention, the tensile member may be one of two tensile members. The method then further comprises attaching the other tensile member to the patient's heart, while the exerting of tension on the one tensile member includes twisting the tensile members about one another.

A surgical method in accordance with the present invention treats congestive heart failure. The method may be performed thoracoscopically which is less expensive and less traumatic to the patient than an open-heart surgical technique. The method of the invention is simple and reliable.

BRIEF DESCRIPTION OF THE DRAWINGS

FIG. 1 is a schematic partial longitudinal cross-sectional view of an instrument or device for operating on the heart to improve cardiac function.

FIGS. 2A–2D are schematic views of a person's heart, showing successive steps in a surgical procedure for improving cardiac function, in accordance with the present invention.

DESCRIPTION OF THE PREFERRED EMBODIMENTS

Figure 3A:
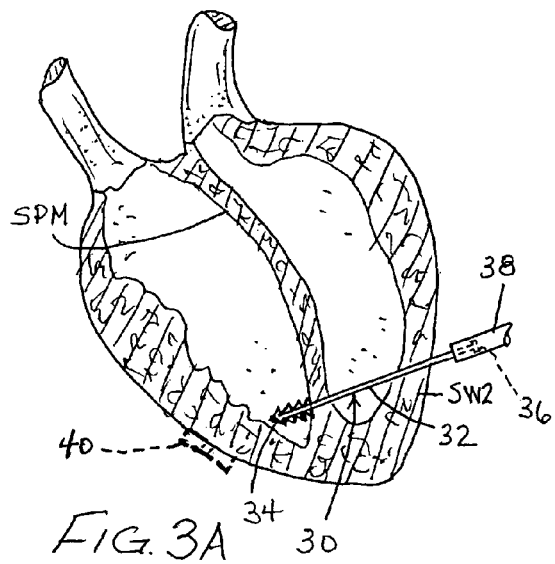
FIGS. 3A and 3B are two schematic cross-sectional views of a patient's heart, showing successive steps in an alternative technique for reducing ventricular volume in accordance with the present invention.

FIG. 1 illustrates a medical device 8 for use in performing surgery as discussed below with reference to FIGS. 2A through 2D to improve cardiac function by reducing the effective volume of the ventricles. The device includes a cardiac clamp 10 in the form of a plurality of elongate prongs or tines 12 connected in a substantially circular or oval configuration to a base 14. Prongs 12 have an inherent spring bias which tends to spread the prongs into a conical configuration as depicted in FIGS. 1 and 2B. Prongs 12 are each provided with at least one tooth 16 which faces inwardly relative to the spread-open conical configuration.

Device 8 further includes an inner tubular member 18 in which clamp 10 is disposed in a collapsed configuration at the onset of a surgical procedure. More specifically, clamp 10 is disposed inside a distal end portion of tubular member 18 prior to an ejection of the clamp by a distally directed motion of a rod 20. Prior to use, rod 20 may be disposed outside of tubular member 18. It is preferable, however, that a rod be disposed partially inside tubular member 18 during initial deployment thereof during a cardiac operation as discussed below.

An elastic band 22 is disposed about tubular member 18 at the distal end thereof. A second tubular member 24 surrounds tubular member 18 for pushing band 22 off of the distal end of tubular member 18 as discussed below.

As illustrated in FIG. 1, a distal end portion of tubular member 18 is inserted through parietal pericardium PP into an intrapericardial space IP surrounding a patient's heart HT. Tubular member 18 may be deployed in an open heart surgical operation or alternatively in a minimally invasive operation. In the latter case, tubular member is inserted through a thoracoscopic cannula or trocar sleeve 26.

Tubular member 18 is inserted from below the heart HT so that the distal end is pointed upwardly substantially parallel to the septum (not shown). After a proper positioning of tubular member 18, rod 20 is pushed in the distal direction, towards an apical portion AP of the heart HT to eject clamp 10, as shown in FIG. 2A. Upon the ejection of clamp 10, prongs 12 automatically spread open under their inherent spring bias to form a conical configuration. The entire instrument assembly is then moved towards heart HT so that the opened clamp 10 surrounds apical portion AP, as illustrated in FIG. 2B. Subsequently, inner tubular member 18 is pushed forward, over clamp 10, as depicted in FIG. 2C. Prongs 12 are pressed inwardly in a camming type action so that teeth 16 bite into the myocardium of heart HT and anchor clamp 10 thereto. Continued forward or distal motion of inner tubular member 18 relative to clamp 10 serves to compress apical portion AP of heart HT, as shown in FIG. 2C. To some extent, prongs 12 pivot about the connecting points to base 14 in response to the camming action of tubular member 18.

After the positioning and partial closure of clamp 10 about the apical portion AP of heart HT, outer tubular member 24 is shifted in the distal direction toward heart, while clamp 10 and inner tubular member 18 are maintained in position about apical heart portion AP. This relative motion serves to slide or push elastic band 22 off of tubular member 18 and onto the closed clamp 10. As illustrated in FIG. 2D, band 22 is left in place on clamp 10 to hold pongs 12 in a partially closed configuration compressing apical portion AP of heart HT and reducing the volume of both ventricles of the heart. The reduced volume makes the pumping action of the heart more efficient and improves blood circulation in individuals suffering from congestive heart failure or left ventricular hypertrophy.

Figure 3B:
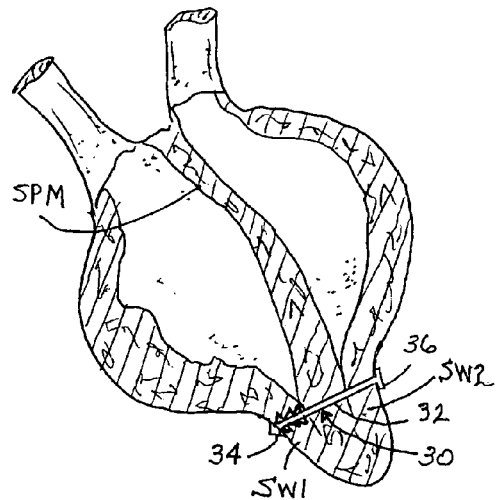

As depicted in FIGS. 3A and 3B, an alternative procedure for reducing ventricular volume utilizes a tack 30 having a substantially rigid shaft 32 and a barbed head 34. Tack 30 is fired into the lower portion of a patient's heart HT so that the tack passes through a first myocardial sidewall SW2, a septum SPM (see FIG. 3A), and a second myocardial sidewall SW1. Barbed head 34 has an arrow-head configuration serving in part to facilitate the passing of tack 30 through the myocardial tissues and also serving to anchor the leading end of the tack to myocardial sidewall SW1. Tack 30 has a predetermined length and a flange 36 at an end of shaft 32 opposite head 34 for collapsing wall SW2 towards septum SPM and wall SW1 and for cooperating with head 34 to clamp the lower portion of heart HT, as indicated in FIG. 3B. Tack 30 may be ejected from a tubular instrument 38 by any known technique including (a) hydraulic or pneumatic pressurization, or (b) manual pushing on a rod (not shown) which extends into tubular instrument 38 and contacts flange 36. Instrument 38 may be used in an open heart surgical procedure or through a cannula or trocar sleeve.

In a modified procedure, it is possible to provide flange 36 on shaft 32 after the insertion of a leading end portion of tack 30, including tack head 34, through the heart HT. A gripper (not shown) pulls back on shaft 32 to compress the lower portion of heart HT after the firing of tack 30. Flange is then attached to shaft 32 via ultrasonic or heat welding.

In another modification of the procedure of FIGS. 3A and 3B, a locking disk 40 is placed against an outer surface of myocardial wall SW1 for engaging barbed head 34 and cooperating therewith to securely fasten tack 30 to the heart HT. Preferably, locking disk 40 is pushed over a portion of barbed head 34 after the emergence of the head from wall SW1. The head has a sufficient number barbs along the length of shaft 32 to provide a "fitting" of the tack to the patient.

Figure 4A:
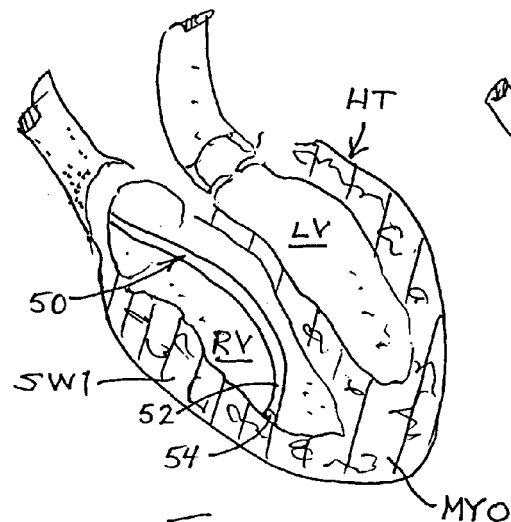
FIGS. 4A–4F are a series of schematic cross-sectional views of a patient's heart, showing successive steps in another alternative technique for reducing ventricular volume in accordance with the present invention.
Figure 4B:
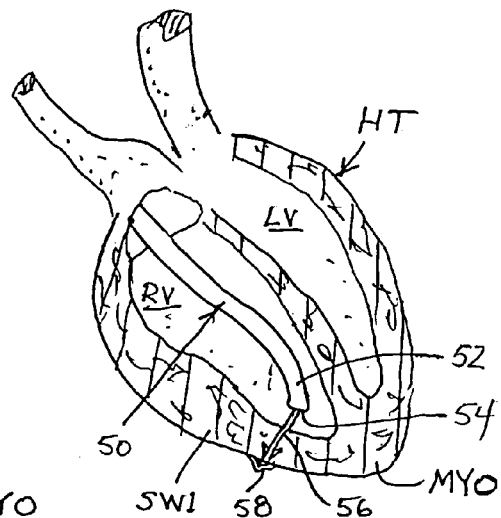
Figure 4C:
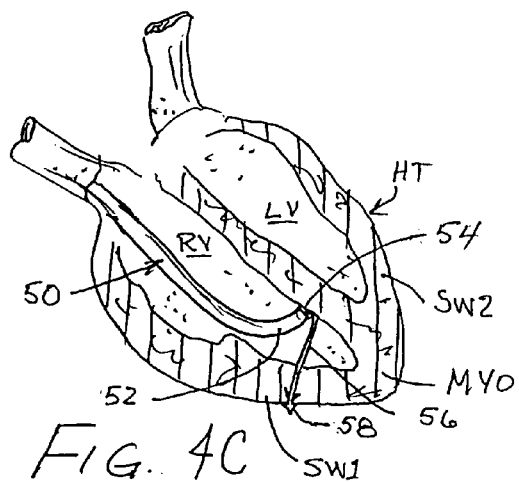
Figure 4D:
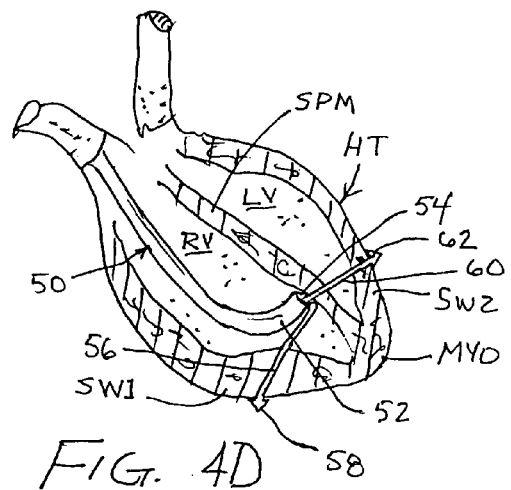
Figure 4E:
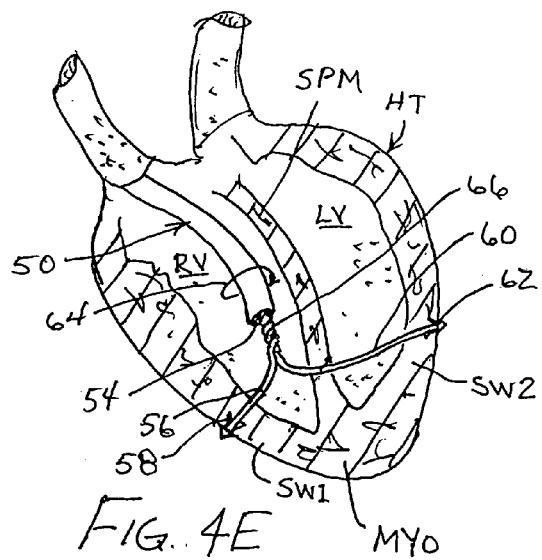
Figure 4F:
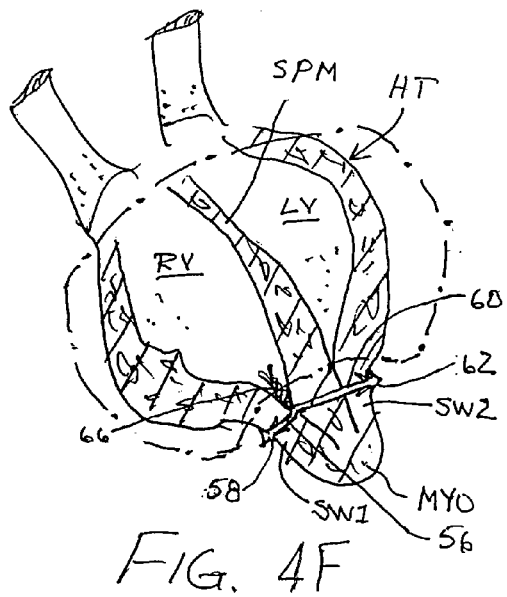

FIG. 4A through 4F illustrate another alternative procedure for reducing ventricular volume. As shown in FIG. 4A, a catheter 50 is inserted through a patient's vascular system into one of the ventricles LV and RV of the patient's heart HT, for example, the right ventricle RV. Catheter 50 has a leading end portion 52 which is steerable to enable a directing of a mouth opening 54 toward a sidewall SW1 of the patient's myocardium MYO. As shown in FIG. 4B, a wire 56 is ejected from catheter 50 through mouth opening 54 into and partially through myocardial sidewall SW1 upon a positioning of the mouth opening adjacent to the sidewall. Wire 56 is provided at a leading end with a plurality of barbs or arrow heads 58 preventing a withdrawal of the wire along its insertion path through myocardial sidewall SW1. Upon an embedding of barbs 58 in myocardial sidewall SW1, catheter 50 is manipulated to steer leading end portion 52 towards cardiac septum SPM, as illustrated in FIG. 4C. Then a second wire 60 is ejected from catheter 50 through mouth opening 54 and septum SPM into and partially through an opposing myocardial sidewall SW2, as depicted in FIG. 4D. Wire 60 is provided at a leading end with a plurality of barbs or arrow heads 62 preventing a detachment of the wire from myocardial sidewall SW2. Upon an embedding of barbs 62 in myocardial sidewall SW2, catheter 50 and wires 56 and 60 are manipulated to twist wires 56 and 60 about one another, as indicated by an arrow 64 and wire coils 66 in FIG. 4E. This twisting action exerts tension on wires 56 and 60 and is performed until sidewalls SW1 and SW2 are drawn sufficiently close to one another, as shown in FIG. 4F, to effectively reduce the volumes of ventricles RV and LV. Wires 56 and 60 are thereafter severed by any practicable technique including but not limited to shearing, laser cutting, etc.

Although the invention has been described in terms of particular embodiments and applications, one of ordinary skill in the art, in light of this teaching, can generate additional embodiments and modifications without departing from the spirit of or exceeding the scope of the claimed invention. For example, with reference to the embodiment of FIGS. 1 and 2A–2D, other mechanisms for closing a compressive device about a lower end of a patient's heart will be apparent to those skilled in the art. Such mechanisms will generally contemplate the conversion of an axially directed force to a compressive force. In one alternative design, instead of pushing tubular member 18 about the expanded clamp 10, a screw mechanism may be used to close, and possibly open, prongs 12. In another alternative design, a cup-shaped clamp has a plurality of relative movable leaves, as in a mechanical iris.

It is to be noted, in addition, that device 8 may be used to place clamp 10 about a part of the heart HT other than apical portion AP. Thus, device 8 may approach the heart HT from a different direction, for example, where it is desired to reduce the effective volume of the left ventricle only.

Prongs 12 may be spring biased to close clamp 10. In that case, the inserting instrument is adapted to spread prongs 12 into a opened configuration in opposition to the action of inherent spring forces. When the opening force is removed, the clamp squeezes the hear muscle and compresses a portion of the heart.

A catch may be provided on prongs 12 for holding band 22 on clamp 10 after the disposition of band about the clamp.

With reference to the embodiment of FIGS. 4A–4F, it is to be noted that other inserts or implants may be delivered to the patient's heart intravascularly via a catheter for purposes of reducing ventricular volume. For example, a balloon may be inserted in a collapsed configuration into a ventricle and inflated with saline solution to decrease the effective volume of the ventricle. The balloon is made of resilient material capable of stretching deformation under systolic pressures. The balloon may be provided on at least one side with projecting barbs for anchoring the balloon to the bottom of the ventricle.

Accordingly, it is to be understood that the drawings and descriptions herein are proffered by way of example to facilitate comprehension of the invention and should not be construed to limit the scope thereof.

What is claimed is:

1. A method for improving cardiac function, comprising: inserting a tensile member into a patient; and
inserting said tensile member into the patient's heart so as to bring opposite walls of each ventricle of the heart into contact with one another to thereby constrict and close off lower portions of both ventricles of the heart.

2. The method defined in claim 1, further comprising anchoring said tensile member to opposing myocardial sidewalls.

3. The method defined in claim 2 wherein the anchoring of said tensile member including placing a flanged element of said tensile member in contact with myocardial tissues.

4. The method defined in claim 2 wherein said the anchoring of said tensile member includes placing a barbed element in contact with myocardial tissues.

5. The method defined in claim 1 wherein said tensile member is a tack, the inserting of said tack including ejecting said tack from a tubular member.

6. The method defined in claim 5 wherein the inserting of said tack includes aiming said tack at an outer surface of the heart.

7. The method defined in claim 1 wherein the inserting of said tensile member includes passing said tensile member through a trocar sleeve or cannula.

8. The method defined in claim 1 wherein the inserting of said tensile member includes:
inserting a catheter into a ventricle of the patient's heart;
ejecting said tensile member from said catheter into the patient's myocardium so that said tensile member is anchored to the myocardium; and
exerting tension on said tensile member to pull opposing walls of the patient's heart towards one another so as to compress and close off lower portions of both ventricles of the heart.

9. A method for reducing ventricular volume, comprising:
inserting a flexible catheter into a ventricle of a patient's heart;
deploying a cardiac insert or implant from a leading end of said catheter; and
disposing said cardiac insert or implant in the patient's heart to bring opposite walls of at least one ventricle of the heart into contact with one another to thereby reduce the volume of the at least one ventricle of the patient's heart.

10. The method defined in claim 9 wherein said cardiac insert or implant is a tensile member, further comprising attaching said tensile member to the patient's heart, and exerting tension on said tensile member to draw the walls of the at least one ventricle towards one another.

11. The method defined in claim 10 wherein said tensile member is provided with at least one barb at a leading end, the attaching of said tensile member to the patient's heart including embedding said barb in the patient's heart.

12. The method defined in claim 10 wherein said tensile member is one of two tensile members, further comprising attaching the other tensile member to the patient's heart, the exerting of tension on said one of said tensile members including twisting the tensile members about one another.

13. The method defined in claim 9 wherein said catheter is inserted into the patient through the vascular system of the patient.

14. A method for reducing ventricular volume, comprising:
inserting a catheter into a ventricle of a patient's heart;
deploying a cardiac insert or implant from a leading end of said catheter while said leading end is disposed in the patient's heart; and
disposing said cardiac insert or implant in the patient's heart to bring opposite walls of at least one ventricle of the heart into contact with one another to thereby reduce the volume of the at least one ventricle of the patient's heart.

15. The method defined in claim 14 wherein said cardiac insert or implant is a tensile member, further comprising attaching said tensile member to the patient's heart, and exerting tension on said tensile member to draw the walls of the at least one ventricle towards one another.

16. The method defined in claim 15 wherein said tensile member is provided with at least one barb at a leading end, the attaching of said tensile member to the patient's heart including embedding said barb in the patient's heart.

17. The method defined in claim 15 wherein said tensile member is one of two tensile members, further comprising attaching the other tensile member to the patient's heart, the exerting of tension on said one of said tensile members including twisting the tensile members about one another.

18. The method defined in claim 14 wherein said catheter is inserted into the patient through the vascular system of the patient.

19. A method for reducing ventricular volume, comprising:
inserting a catheter through a patient's vascular system into a ventricle of the patient's heart;
deploying a cardiac insert or implant from a leading end of said catheter; and
disposing said cardiac insert or implant in the patient's heart to bring opposite walls of at least one ventricle of the heart into contact with one another to thereby reduce the volume of the at least one ventricle of the patient's heart.

20. The method defined in claim 19 wherein said cardiac insert or implant is a tensile member, further comprising attaching said tensile member to the patient's heart, and exerting tension on said tensile member to draw walls of the patient's heart towards one another.

* * * * *